(12) United States Patent
Beinhocker

(10) Patent No.: US 8,653,971 B2
(45) Date of Patent: Feb. 18, 2014

(54) SENSOR TAPE FOR SECURITY DETECTION AND METHOD OF FABRICATION

(75) Inventor: Gilbert D. Beinhocker, Belmont, MA (US)

(73) Assignee: 3D Fuse Sarl, Geneva (CH)

( * ) Notice: Subject to any disclaimer, the term of this patent is extended or adjusted under 35 U.S.C. 154(b) by 0 days.

(21) Appl. No.: 13/440,376

(22) Filed: Apr. 5, 2012

(65) Prior Publication Data

US 2013/0187630 A1  Jul. 25, 2013

Related U.S. Application Data

(60) Provisional application No. 61/590,589, filed on Jan. 25, 2012.

(51) Int. Cl.
*G08B 13/00* (2006.01)

(52) U.S. Cl.
USPC .......................................... 340/541

(58) Field of Classification Search
USPC .......................................... 340/541
See application file for complete search history.

(56) References Cited

U.S. PATENT DOCUMENTS

| | | | |
|---|---|---|---|
| 2,311,613 A | 2/1943 | Slayter | |
| 3,320,114 A | 5/1967 | Schulz | |
| 3,634,845 A * | 1/1972 | Colman | 340/508 |
| 3,714,644 A | 1/1973 | Hellstrom | |
| 3,947,837 A | 3/1976 | Bitterice | |
| 4,095,872 A | 6/1978 | Stieff et al. | |
| 4,118,211 A | 10/1978 | Au Coin et al. | |
| 4,161,348 A | 7/1979 | Ulrich | |
| 4,175,827 A | 11/1979 | McMahon | |
| 4,195,907 A | 4/1980 | Zamja et al. | |
| 4,217,488 A | 8/1980 | Hubbard | |
| 4,228,425 A | 10/1980 | Cooke | |
| 4,234,875 A | 11/1980 | Williams | |
| 4,297,684 A | 10/1981 | Butter | |
| 4,318,088 A * | 3/1982 | Hunter | 340/541 |
| 4,367,460 A | 1/1983 | Hodara | |
| 4,447,123 A | 5/1984 | Page et al. | |
| 4,488,269 A | 12/1984 | Robinson et al. | |
| 4,526,752 A | 7/1985 | Perlman et al. | |
| 4,538,527 A | 9/1985 | Kitchen | |
| 4,573,202 A | 2/1986 | Lee | |
| 4,603,252 A | 7/1986 | Malek et al. | |
| 4,772,092 A | 9/1988 | Hofer et al. | |
| 4,801,213 A | 1/1989 | Frey et al. | |
| 4,867,820 A | 9/1989 | Jacobson et al. | |

(Continued)

*Primary Examiner* — Charlie Peng

(74) *Attorney, Agent, or Firm* — Preti Flaherty Beliveau & Pachios LLP

(57) ABSTRACT

A sensor in the form of an elongated flexible tape has a signal path made from electrical wire or optical fiber which extends between one end and another end of the tape. The electrical wires or optical fibers are disposed in spaced relation across the width and along the length of the tape and are terminated in connectors at the endpoints of the tape. The connectors may be integrated into a signal detector to interface with communication links. The tape is a material that is non-conductive and in which the wires or optical fibers may be woven, disposed or embedded in some manner. One or more layers of flexible material can be laminated on respective sides of the sensor tape to provide a robust laminated or bonded structure that can be rolled and unrolled from a reel. An adhesive layer and a removable layer can be provided to protect the adhesive layer prior to use. An overcoat of outer layer resin may be applied.

8 Claims, 13 Drawing Sheets

(56) References Cited

U.S. PATENT DOCUMENTS

| | | | | |
|---|---|---|---|---|
| 4,908,510 | A | 3/1990 | Huggins et al. | |
| 4,931,771 | A | 6/1990 | Kahn | |
| 4,935,723 | A | 6/1990 | Vallance | |
| 4,972,176 | A | 11/1990 | Vallance | |
| 5,003,374 | A | 3/1991 | Vokoun, III | |
| 5,049,855 | A | 9/1991 | Slemon et al. | |
| 5,081,363 | A | 1/1992 | Tetzlaff et al. | |
| 5,119,862 | A | 6/1992 | Maimets et al. | |
| 5,180,060 | A | 1/1993 | Forti et al. | |
| 5,194,847 | A | 3/1993 | Taylor et al. | |
| 5,309,533 | A | 5/1994 | Bonniau et al. | |
| 5,323,011 | A | 6/1994 | Suter et al. | |
| 5,355,208 | A | 10/1994 | Crawford et al. | |
| 5,359,416 | A | 10/1994 | Mueller | |
| 5,568,124 | A | 10/1996 | Joyce et al. | |
| 5,592,149 | A | 1/1997 | Alizi | |
| 5,609,952 | A | 3/1997 | Weiss | |
| 5,648,724 | A * | 7/1997 | Yankielun et al. | 324/533 |
| 5,769,232 | A | 6/1998 | Cash et al. | |
| 5,790,025 | A | 8/1998 | Amer et al. | |
| 5,808,554 | A * | 9/1998 | Shuminov | 340/604 |
| 5,918,268 | A | 6/1999 | Lukas et al. | |
| 6,002,501 | A | 12/1999 | Smith et al. | |
| 6,065,870 | A | 5/2000 | Nunez | |
| 6,213,167 | B1 | 4/2001 | Greenland | |
| 6,487,895 | B2 | 12/2002 | Brooker et al. | |
| 6,556,138 | B1 | 4/2003 | Sliva et al. | |
| 6,879,257 | B2 | 4/2005 | Hisano | |
| 6,891,470 | B2 | 5/2005 | Bohinc, Jr. | |
| 6,919,803 | B2 | 7/2005 | Breed | |
| 7,098,444 | B2 | 8/2006 | Beinhocker | |
| 7,098,784 | B2 | 8/2006 | Easley et al. | |
| 7,137,525 | B2 | 11/2006 | Gibney | |
| 7,211,783 | B2 | 5/2007 | Beinhocker | |
| 7,352,284 | B2 | 4/2008 | Krill | |
| 7,394,060 | B2 * | 7/2008 | Beinhocker | 250/227.14 |
| 7,482,924 | B1 * | 1/2009 | Beinhocker | 340/555 |
| 7,595,452 | B2 | 9/2009 | Kirstein et al. | |
| 7,702,358 | B2 | 4/2010 | Meyers | |
| 7,706,641 | B2 * | 4/2010 | Murphy et al. | 385/13 |
| 7,731,517 | B2 * | 6/2010 | Lee et al. | 439/271 |
| 2002/0089434 | A1 | 7/2002 | Ghazarian | |
| 2003/0151509 | A1 | 8/2003 | Iannotti et al. | |
| 2003/0174059 | A1 | 9/2003 | Reeves | |
| 2003/0193032 | A1 | 10/2003 | Marshall | |
| 2004/0037091 | A1 | 2/2004 | Guy | |
| 2004/0046660 | A1 | 3/2004 | Ando | |
| 2004/0047142 | A1 | 3/2004 | Goslee | |
| 2004/0056767 | A1 | 3/2004 | Porter | |
| 2006/0151656 | A1 | 7/2006 | Gallagher et al. | |
| 2006/0244616 | A1 * | 11/2006 | Hill | 340/604 |
| 2007/0001844 | A1 | 1/2007 | Krill | |
| 2008/0211669 | A1 | 9/2008 | Dagher et al. | |
| 2009/0115607 | A1 * | 5/2009 | Beinhocker | 340/541 |
| 2010/0097215 | A1 | 4/2010 | Locher | |
| 2010/0170616 | A1 * | 7/2010 | Boss et al. | 156/71 |
| 2012/0133507 | A1 * | 5/2012 | Bangera et al. | 340/540 |

* cited by examiner

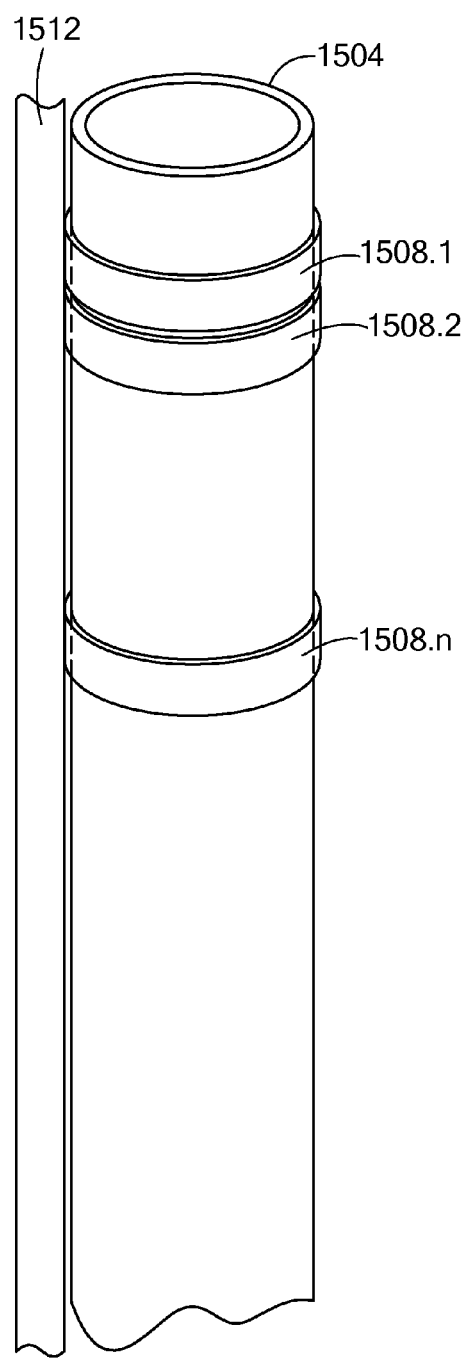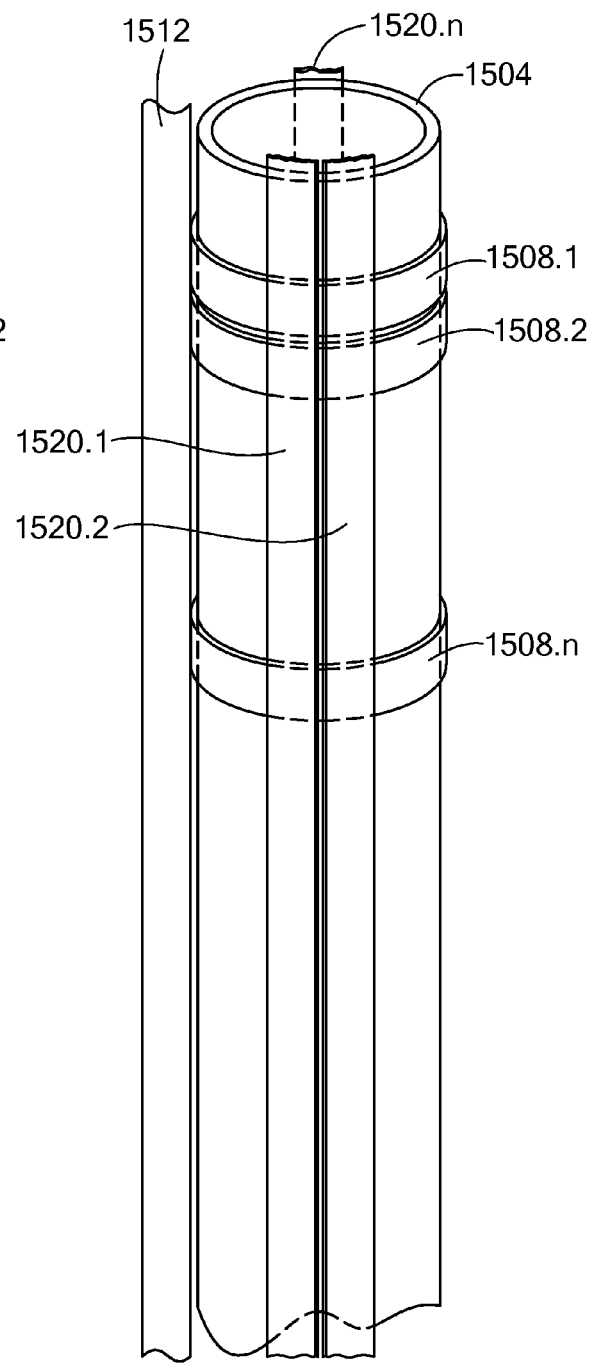
*FIG. 15*  *FIG. 16*

SENSOR TAPE FOR SECURITY DETECTION AND METHOD OF FABRICATION

CROSS REFERENCE TO RELATED APPLICATIONS

This application claims the benefit under 35 U.S.C. §119(e) of U.S. Provisional Patent Application No. 61/590,589, entitled "3 Dimensional Fuse And Method Of Fabrication," filed on Jan. 25, 2012, which is herein incorporated by reference in its entirety for all purposes.

This application is related to a number of issued patents and pending patent applications, in the name of the inventor of the present application, that relate to tamper proof containers and other enclosures and security systems for containers, enclosures, pipelines and other structures. The issued U.S. patents are: U.S. Pat. Nos. 7,211,783; 6,995,353; 7,394,060; 7,608,812; 7,332,728; 7,098,444; 7,482,924; 7,619,226; 7,856,157 and 7,924,166.

STATEMENT REGARDING FEDERALLY SPONSORED RESEARCH OR DEVELOPMENT

N/A

BACKGROUND OF THE INVENTION

As is known, in order to detect an intrusion into, or out of, a protected volumetric space, a sensor sheet is provided to enclose the volume of interest which has a continuous electrical or optical signal path disposed in the sheet and substantially encompassing the full extent thereof. An electrical signal, in the case of a wire path, or an optical signal, in the case of an optical fiber path, is introduced to one end of the signal path, and the signal is received at the opposite end of the signal path. The presence of a signal indicates a normal or non-alarm state. In the event of a break or other interruption in the signal path, the loss or diminution of the signal is detected and signifies an alarm condition. In the case of an optical fiber signal path, the optical fiber can be sensitive to incident nuclear radiation that causes a reduction in the amplitude and/or characteristics of the optical signal and which can be detected as an indication of an alarm condition.

Current fabrication techniques for installation of sensor sheets involve first applying a resin layer to the surface of the object to be enclosed, e.g., the interior walls of a cargo container or the outer surface of a pipeline. The resin must be allowed to dry to a certain point and then, within a specified time window, i.e., before the resin hardens, the sensor sheet is to be laid on top. A top layer of resin is thereafter applied and allowed to dry to hold fast the sensor sheet in a protective sandwich construction.

In some applications, for example, gas wells, it is not as much of an issue of security but, rather, one of locating a failure in order to quickly make a repair. Gas wells usually include a pipeline casing, however, when the casing is compromised and gas escapes through the ground to the surface, known as "surface casing vent flow and gas migration," it must be repaired. The release of gas has to be stopped as soon as detected, and while it is relatively easy to detect that gas is leaking, identifying the location of the leak along the length of the casing is a much bigger challenge.

A known detection method runs an acoustic instrument down the well that detects noise patterns that are plotted on a graph as the instrument is slowly withdrawn. Any variances of sound, such as pitch, will be used to identify the location of the leak. When a leak location has been determined, a hole is made in the casing and cement is inserted in to stop the gas leak. The instrument, however, must be run again to assure that the hole has been plugged but a relatively large retry rate is necessary to finally seal the leak. The delays associated with this process of determining where the leak is located translate into lost operating time, the incurring of repair costs and, therefore, decreased revenue for the gas well operator.

There is, therefore, a need for providing a mechanism that will detect an intrusion or extrusion with respect to a pipeline container or enclosure and that can be applied quickly, easily and economically and that will be able to provide detection coverage for irregularly as well as regularly shaped volumetric enclosed structures. Additionally, determining a location of a defect is also needed in order to apply a repair.

BRIEF SUMMARY OF THE INVENTION

In one embodiment, a sensor security detector tape includes a material strip with predetermined width and length and first and second ends. At least one signal path is provided in the material strip where each signal path has a first end and a second end. First and second connectors are coupled to the first and second ends, respectively, of the signal paths.

In another embodiment, a method of fabricating a sensor security detector tape includes providing a material strip having a predetermined width and a predetermined length and first and second ends and coupling at least one signal path to the material strip, where each at least one signal path has a first end and a second and. Subsequently, first and second connectors are coupled to the first and second ends, respectively, of the signal paths.

The signal paths may be either wire or optical fiber.

BRIEF DESCRIPTION OF THE SEVERAL VIEWS OF THE DRAWINGS

Various aspects of at least one embodiment of the present invention are discussed below with reference to the accompanying figures. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, not every component may be labeled in every drawing. The figures are provided for the purposes of illustration and explanation and are not intended as a definition of the limits of the invention. In the figures:

FIG. 15 is an application of a sensor tape in accordance with an embodiment of the present invention; and FIG. 16 is an application of a sensor tape in accordance with an embodiment of the present invention.

DETAILED DESCRIPTION OF THE INVENTION

Figure 1:
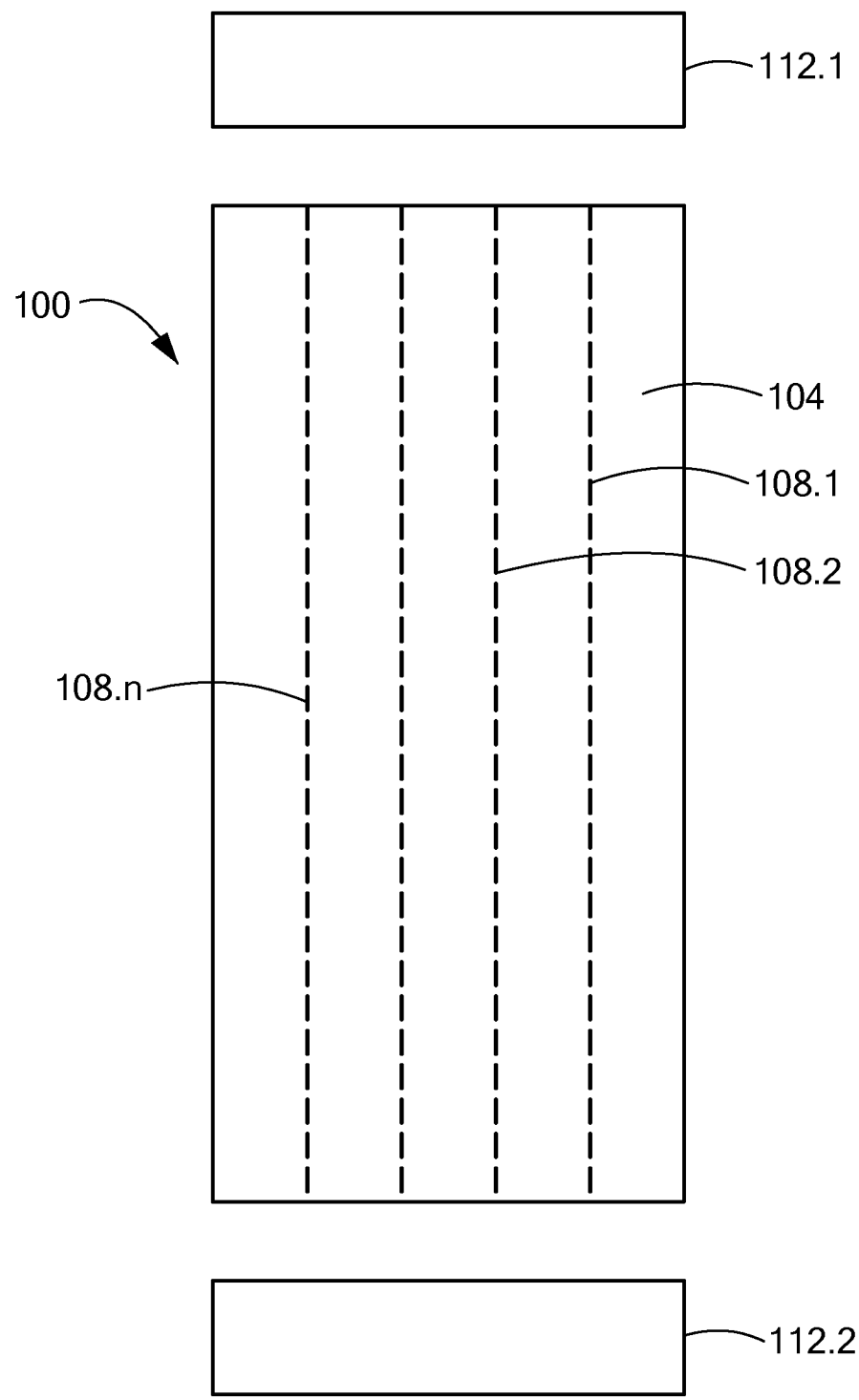
FIG. 1 is a schematic representation of a sensor tape structure in accordance with an embodiment of the present invention.

This application claims the benefit under 35 U.S.C. §119(e) of U.S. Provisional Patent Application No. 61/590,589, entitled "3 Dimensional Fuse And Method Of Fabrication," filed on Jan. 25, 2012, which is herein incorporated by reference in its entirety for all purposes.

Further, each of U.S. Pat. Nos. 7,211,783; 6,995,353; 7,394,060; 7,608,812; 7,332,728; 7,098,444; 7,482,924; 7,619,226; 7,856,157 and 7,924,166 is incorporated by reference herein in its entirety for all purposes.

In the following detailed description, numerous specific details are set forth in order to provide a thorough understanding of the embodiments of the present invention. It will be understood by those of ordinary skill in the art that these embodiments of the present invention may be practiced without some of these specific details. In other instances, well-known methods, procedures, components and structures may not have been described in detail so as not to obscure the embodiments of the present invention.

Prior to explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Embodiments of the present invention relate to a an elongated flexible sensor security detector tape having a signal path provided therein by electrical wire or optical fiber and which extends between one end of the tape to the other end of the tape. In one embodiment, as will be described in more detail below, a plurality of electrical wires or optical fibers are disposed in the tape in a spaced relation, e.g., parallel to one another, across the width of the tape and extending along the length of the tape. The tape may include a non-conductive material in which the wires or optical fibers are woven or otherwise disposed in, for example, a polyester material. Protective layers of flexible material may be laminated on respective sides of the sensor tape to provide a laminated structure that is robust and that can be readily rolled and unrolled from a reel for efficiency of transport and for installation on a structure to be protected, e.g., by encapsulating any configuration of volumetric space, such as a pipeline, by spin-wrapping. Spin-wrapping is a well understood technique in the pipeline industry used to apply an insulation material to pipes in order to provide a solid coating, for example, a thermal-protecting coating.

Additionally, after application by spin-wrapping, a protective resin coating can be applied over the sensor tape segments as an additional protective layer. Tuffset P resin, available from Isothane Ltd. in the United Kingdom, is one such resin available for this application.

In one embodiment of the present invention, a linear sensor tape segment 100 includes a material strip 104. A plurality of signal paths 108.$n$ are disposed either on, or within, the material strip 104, as shown in FIG. 1. The signal paths 108.$n$ may comprise electrical wires for carrying an electrical signal or optical fibers for carrying an optical signal. In one embodiment, the material strip 104 may be, but is not limited to, a non-conductive fabric material in which the wires or optical fibers may be woven or otherwise disposed. Here, the plurality of signal paths 108.$n$ are spaced across the width of the material strip 104, generally parallel to one another, but not electrically or optically coupled to one another. The electrical wires may or may not be individually insulated. The resolution distance between the signal paths 108.$n$ in the material strip 104 can be chosen as needed and, in one embodiment, is approximately 0.25 inches, although almost any distance as will fit the requirements can be chosen. The length of the linear sensor tape segment 100 may be cut to fit the particular application. Once cut to the desired length, two bridging connectors 112.1, 112.2 are coupled, respectively, to the ends of the material strip 104. The function of the bridging connectors 112.1, 112.2 will be described below.

Figure 2:
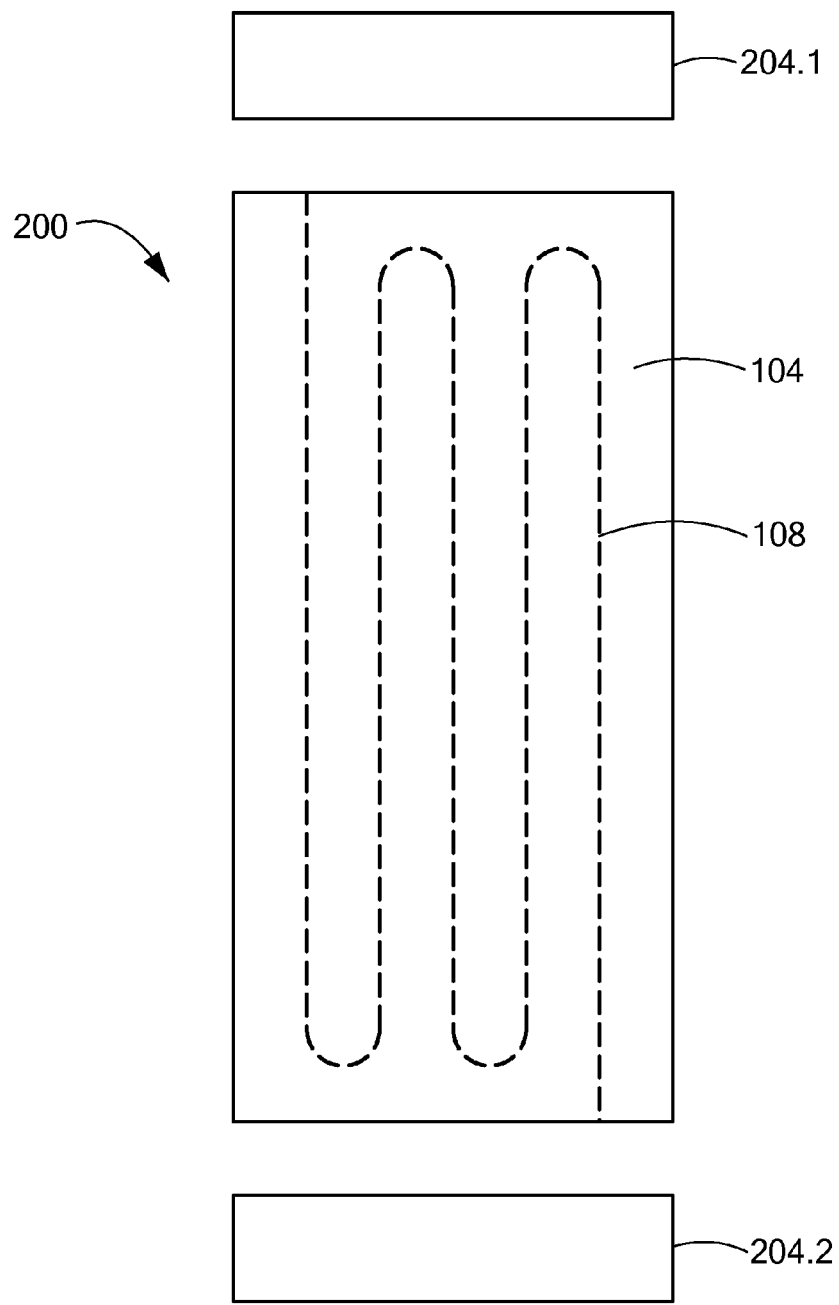
FIG. 2 is a schematic representation of a sensor tape structure in accordance with another embodiment of the present invention.

In another embodiment of the present invention, as shown in FIG. 2, a sinuous sensor tape segment 200 includes the material strip 104 with a sole signal path 108 comprising an electrical wire or an optical fiber. Here, the sole signal path 108 is distributed in a sinuous pattern across the width of the material strip 104. Two terminating connectors 204.1, 204.2 are coupled, respectively, to the ends of the material strip 104. The function of the terminating connectors 204.1, 204.2 will be described below.

Figure 3A:
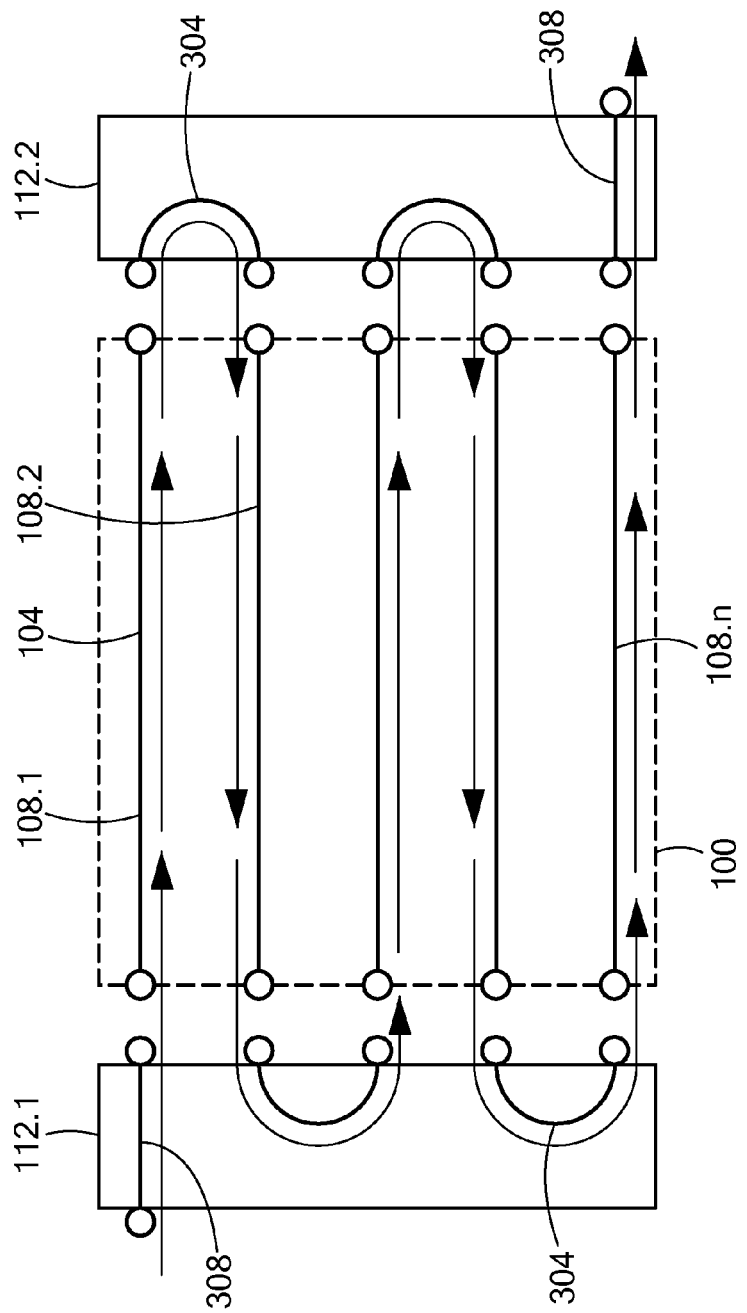
FIGS. 3A and 3B are electrical schematic representations of the sensor tape structures of FIGS. 1 and 2.

Referring now to FIG. 3A, each bridging connector 112.$n$ includes a plurality of jumper links 304 to electrically, or optically, couple the signal paths 108.$n$ into a single continuous signal path, as represented by the arrows. The bridging connector 112 is provided at the end of each linear sensor tape segment 100 to bridge, i.e., interconnect, the signal paths 108.$n$, i.e., the wires or optical fibers in the linear sensor tape segment 100 to provide a single continuous signal path through the linear sensor tape segment 100 from one end to the other. The jumper links 304 are arranged to correspond with the signal paths 108.$n$ and the bridging connector 112 would be sized to match the width of the fabric 104. The bridging connector 112 also includes a pass-through link 308 that couples the single continuous signal path either to a signal source, a next sensor tape segment or a signal sensing system.

Figure 3B:
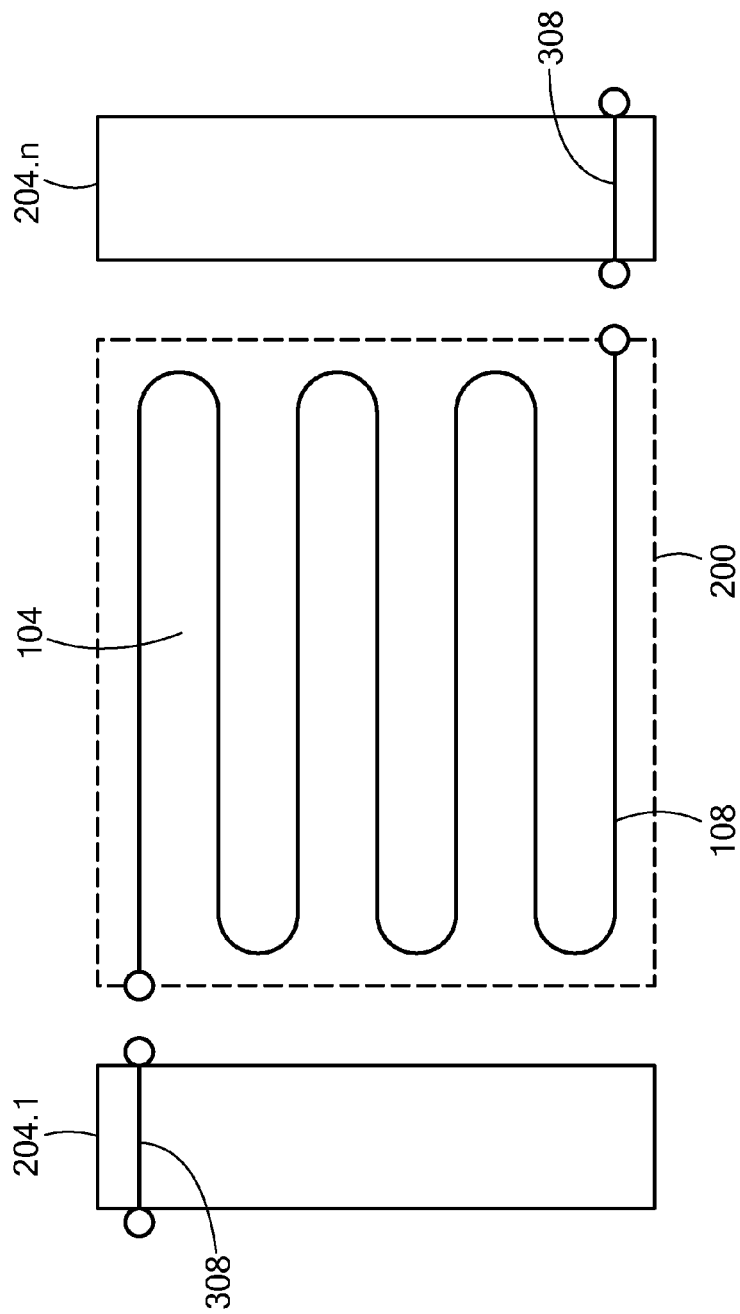

The terminating connector 204 includes a pass-through link 308, as shown in FIG. 3B, to provide an interface to the sole signal path 108. Of course, the terminating connector 204 is sized to match the material strip 104 and couple to the corresponding end of the sole signal path 108.

The connectors 112, 204 may be Flexible Printed Circuit (FPC) type connectors as available from many different vendors such as Tyco or Molex. As known to one of ordinary skill in the art, an FPC type connector will clamp onto the sensor tape segment and couple to the signal paths.

Figure 4:
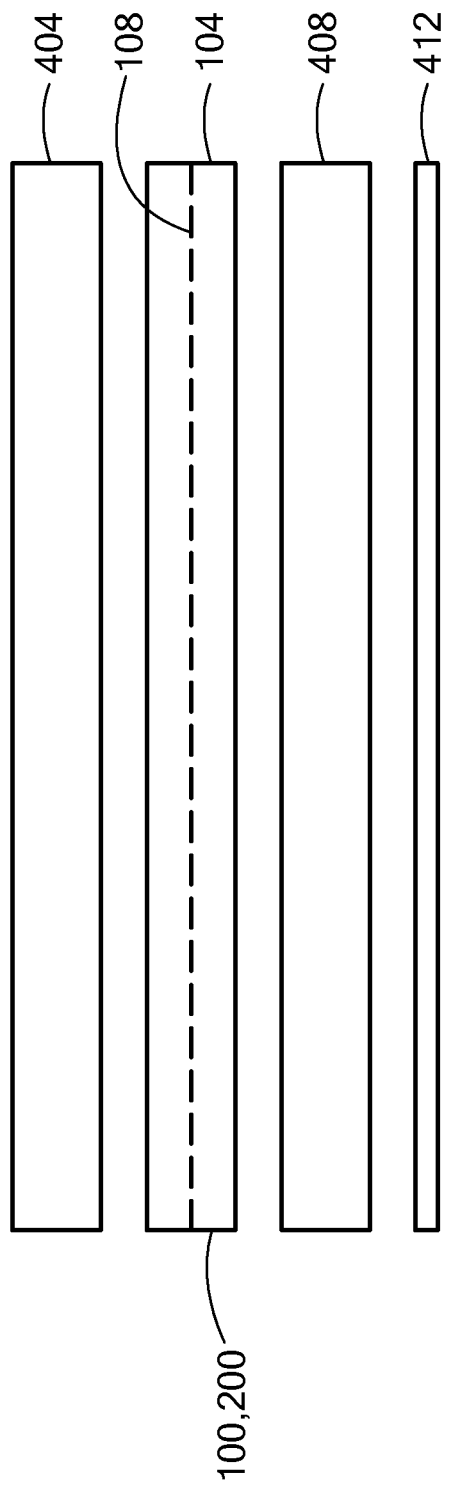
FIG. 4 is an exploded view of a sensor tape structure in accordance with an embodiment of the present invention.

A number of protective layers 404, 408 of a flexible material may be laminated on respective sides of either of the sensor tape segments 100, 200 to provide a laminated structure, as shown in FIG. 4 (in exploded view). Here, the signal path 108 is shown as being provided within the material strip 104 merely for ease of explanation although other embodiments as described herein are also applicable. The protective layer or layers 404, 408 are provided to protect the inner sensor tape segment 100, 200. The one or more protective layers 404, 408 of suitable material can be laminated or otherwise secured to each side of the sensor tape segment 100, 200 with the properties needed to suit a particular installation's requirements.

The protective layers 404, 408 may be, for example, silicone rubber or plastic and may be attached to respective sides of the sensor tape segment 100, 200 by any one of a number of mechanisms, including, but not limited to, gluing with an adhesive, heat bonding, pressure bonding, etc. The protective layers 404, 408 may be waterproof and resistant to other environmental and other contaminants to which they may be exposed. The protective layers may also have releasable layers of paper to be peeled off prior to application.

In one embodiment, an adhesive outer surface 412 may be provided to allow for initial bonding to the surface of, for example, a pipe, during installation of the tape, where the surface may or may not have a sheen layer of anti-corrosion film already applied.

One of skill in the art will understand that the number of protective layers 404, 408 may vary depending upon the needs of the application. Further, various combinations and sub-combinations of the protective layers 404, 408 in conjunction with the adhesive layer 412 are contemplated, for example, where the adhesive layer 412 is applied to the sensor tape 100, 200 without there being a protective layer 408 disposed between. In addition, a sensor tape 100, 200 may be "sandwiched" between two adhesive layers 412, with or without, protective layers on either side. Still further, a structure with multiple layers of sensor tape 100, 200 is also contemplated as being within the scope of this invention.

Figure 9:
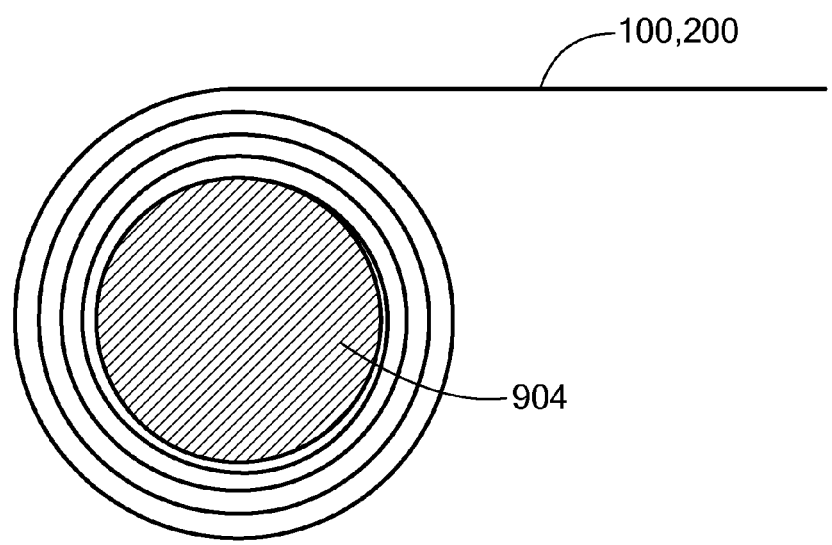
FIG. 9 is a representation of a spool of sensor tape in accordance with an embodiment of the present invention.

The sensor tape segment 100, 200 is fabricated in lengths suitable for spin wrapping or other application onto an enclosure or protected space. In one embodiment, the tape segment 100, 200 is about 5-7 inches wide and about 250-300 feet long. The sensor tape 100, 200, with or without protective layers 404, 408, or an adhesive layer 412, may be provided on a spool 904, as shown in FIG. 9. Of course, one of ordinary skill will understand that any necessary release layers would be provided in order to allow for the unrolling of the sensor tape 100, 200 when being applied, as described below.

Figure 5A:
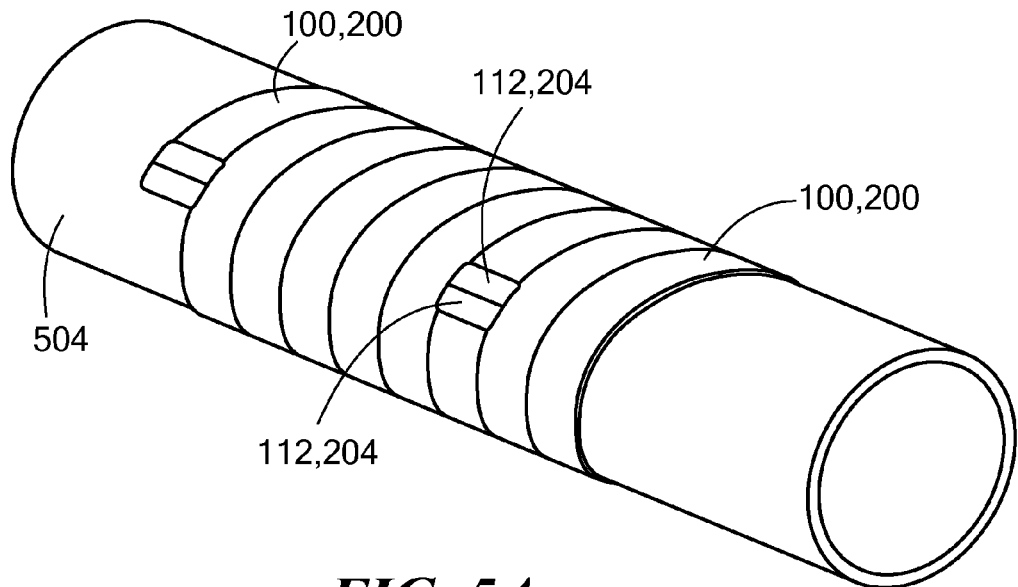
FIGS. 5A and 5B are representations of applications of an embodiment of the sensor tape structure in accordance with the present invention.

In one application, the sensor tape segments 100, 200 are wrapped around, for example, a pipeline or pipe section 504, as shown in FIG. 5A, to provide an effectively continuous wrapping. The sensor tape segments 100, 200 may be helically wrapped around the pipe section 504. The connectors 112, 204 of sequentially adjacent sensor tape segments 100, 200 are interconnected to provide a continuous signal path through the multiple tape segments. The wrapping can be guided on the irregular surface of a pipe by sensors to ensure edge-to-edge alignment of the tape to ensure a smooth continuous wrap. For example, a stripe or marker can be placed along the longitudinal edge of the tape and can be visually, by person or machine, monitored to align the tape segments by optical recognition and feedback as would be understood by those of ordinary skill in the art. In addition, a raised edge may be provided on the tape segment and used as an indicator to align segments when being applied.

Figure 5B:
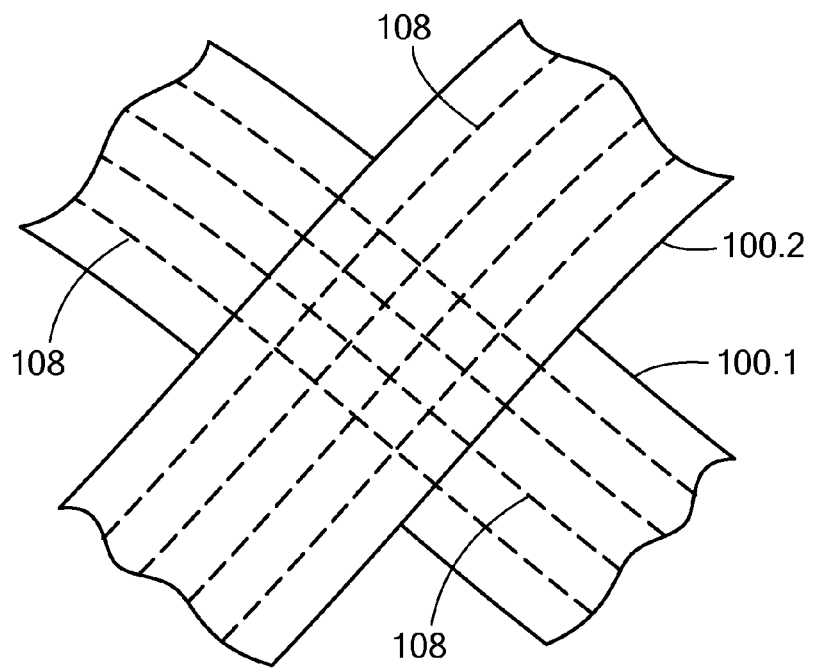

In another application, by applying a second sensor tape segment over a first tape segment an effective resolution can be improved. Referring to FIG. 5B, for example, a first sensor tape segment 100.1 is placed, e.g., wrapped, in a first orientation about the item and a second sensor tape segment 100.2 is wrapped in a second orientation different from the first orientation, about a portion of the first sensor tape segment 100.1. As a result, a portion of the plurality of parallel signal paths 108 in the second sensor tape segment 100.2 cross a portion of the plurality of parallel signal paths 108 in the first sensor tape segment 100.1. Thus, a grid of signal paths is established. Where the signal paths are ¼ inch apart, if applied at right angles to one another, an effective resolution of ¹⁄₁₆ square inch can be had as shown in FIG. 5B. Still further, the second tape segment 100.2 may be applied at any angle, not just a right angle, to the first tape segment 100.1.

Thus, if each of the multiple layers is geometrically offset from the others by a predetermined distance, the effective detection resolution is increased, i.e., the density of wires per square area is increased. Accordingly, any desired cost-effective detection resolution can be established. In principle, multiple offset layers can theoretically reduce the aperture of resolution to such a small opening that an effectively "solid wall" is provided that detects a breach, i.e., either an intrusion or extrusion, of any size.

Alternately, a single tape segment could be wrapped back on itself to effectuate the same grid of signal paths.

The sensor tape segment 100, 200 of the present invention can be readily installed in the field by spin wrapping onto pipe sections as they are being constructed into a pipeline. Alternatively, the sensor tape segment 100, 200 can be factory installed on sections of the pipe before it is transported to an installation site. This would likely be more economical for making smaller pipes such as those found in chemical plants or nuclear plants, for example.

An overcoating of polyurethane or other suitable material can be applied over the tape segments 100, 200 after being wrapped about the pipe 504 to protect against wear, abrasion and other adverse or damaging conditions to which the pipe 504 may be exposed.

Alternate embodiments of the sensor tape will now be described. It is understood that the following embodiments may be implemented in the multi-layer tape described above.

Figure 11A:
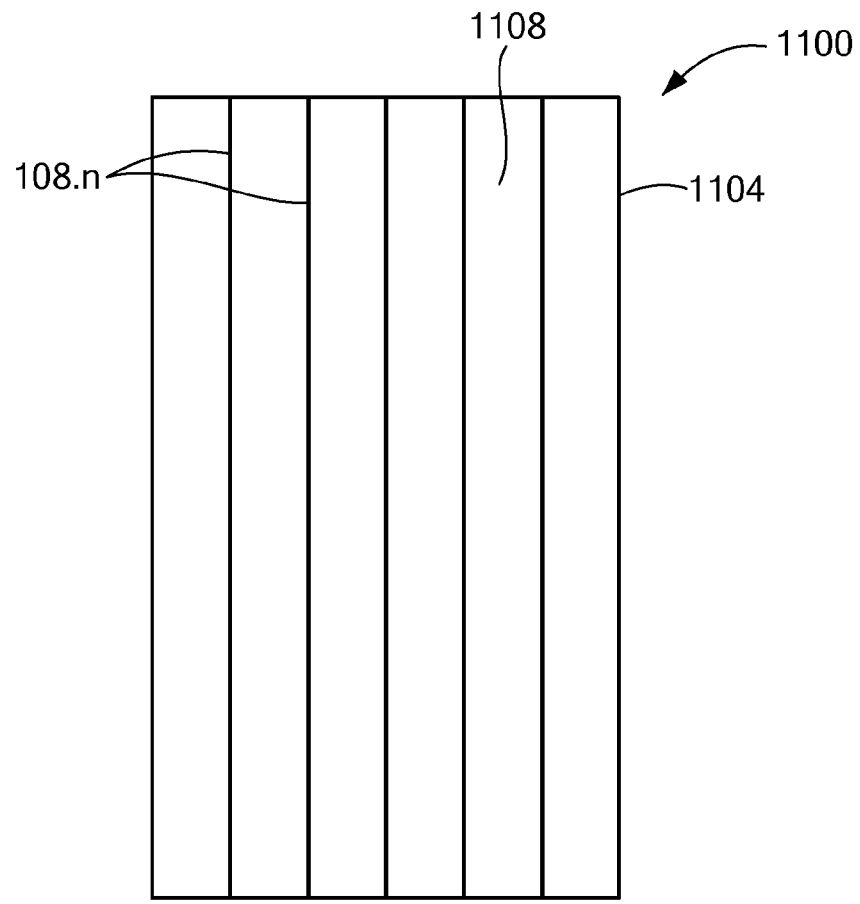
FIGS. 11A and 11B are representations of a sensor tape in accordance with an embodiment of the present invention.
Figure 11B:
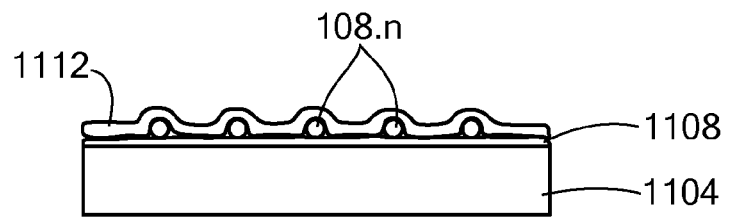

Referring now to FIGS. 11A and 11B, a sensor tape segment 1100 includes a single-ply tape strip 1104 such as, for example, duct tape, having adhesive material 1108 disposed on a surface of the single-ply tape strip 1104. The single-ply tape strip 1104 could also be, for example, a plastic or rubber material with the adhesive material 1108 disposed thereon. One of ordinary skill in the art will understand the many mechanisms for applying the adhesive material 1108 in addition to the choices of adhesive depending on desired tackiness, removability, etc. As shown, the parallel signal paths 108.$n$ may placed in the adhesive material 1104. A cross-section side view of the sensor tape segment 1100 is shown in FIG. 11B. The single-ply tape strip 1104 can be of any desired width.

In order to allow for rolling on a reel, to be used with a handheld or mechanized wrapping machine such as used for wrapping packing tape around boxes, a releasable layer 1112 may be provided over the signal paths 108.$n$. The releasable layer 1112 may comprise a thin flexible sheet and adheres to the exposed adhesive material 1108 between the signal paths 108.n. As described above, the signal paths 108.n may be insulated or bare electrical wires or optical fibers with or without protective cover. In addition, a connector 112 can be attached to each end of the sensor tape segment 1100 for interconnecting the wires or fibers as described above.

Figure 12A:
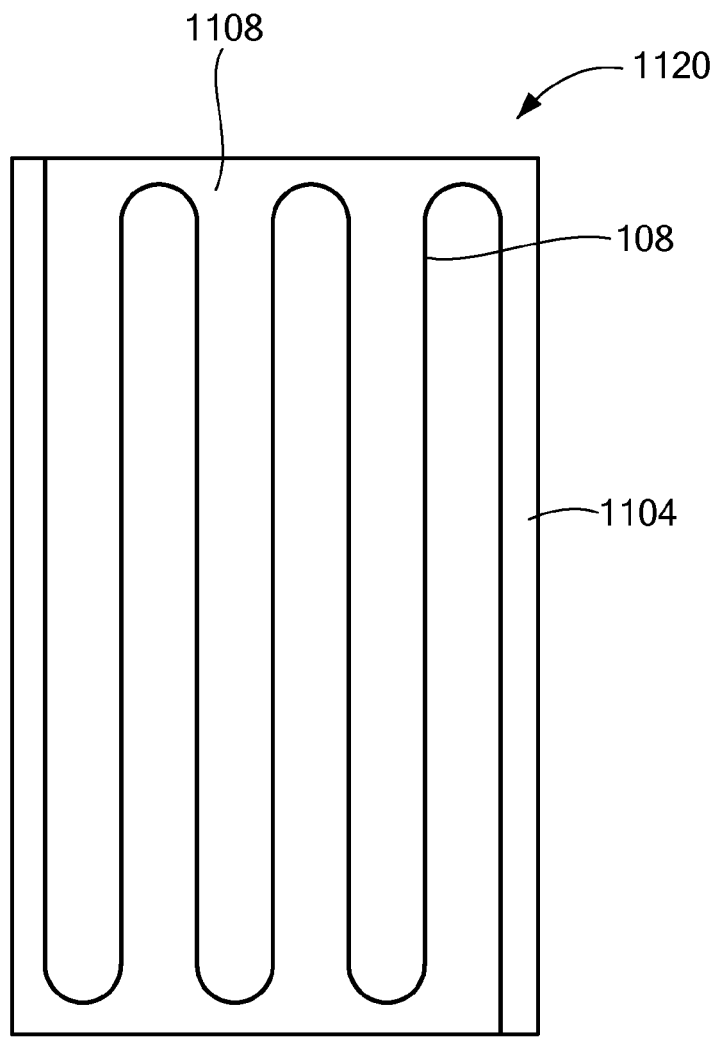
FIGS. 12A and 12B are representations of a sensor tape in accordance with an embodiment of the present invention.
Figure 12B:
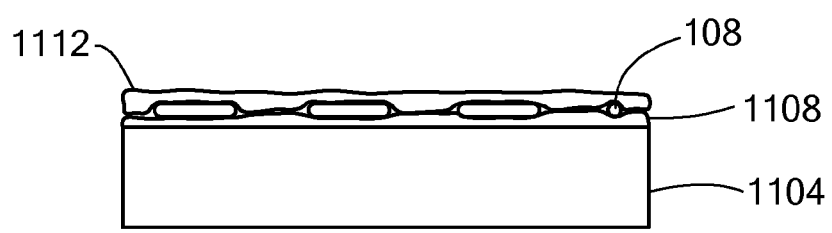

Referring now to FIGS. 12A and 12B, a sensor tape segment 1120, similar to the sensor tape segment 1100, includes a single-ply tape strip 1104 having adhesive material 1108. As shown, instead of parallel signal paths 108.n, a sole sinuous signal path 108 may be placed in the adhesive material 1104. A cross-section side view of the sensor tape segment 1120 is shown in FIG. 12B. Similarly to that already disclosed, a releasable layer 1112 may be provided.

Figure 13:
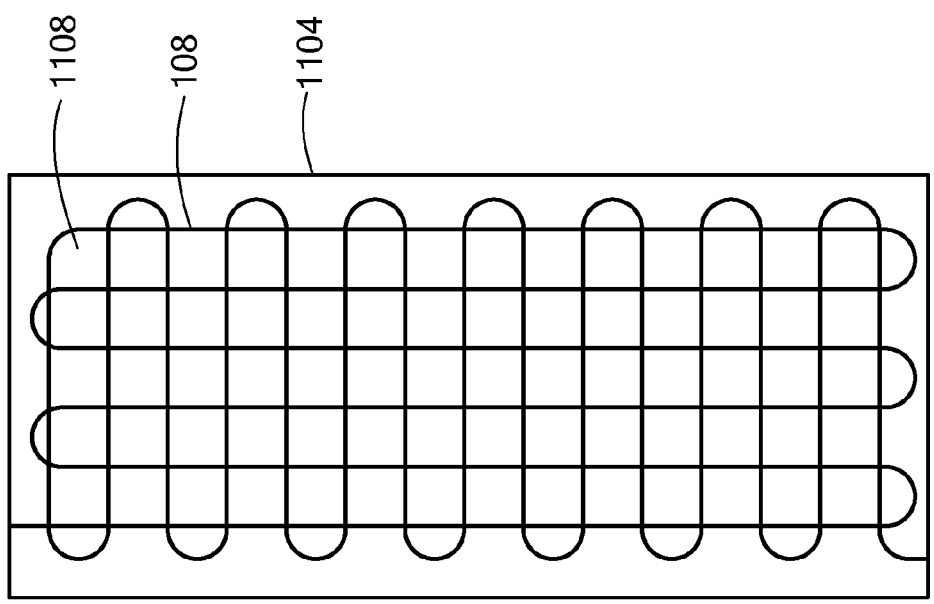

There are variations on the sole signal path where, as shown in FIG. 13, a hybrid approach is used that includes parallel rows with interleaved sinuous paths. Depending upon the spacing, a single path is provided with finer detection resolution as compared to only parallel paths or only a sinuous path.

Figure 14:
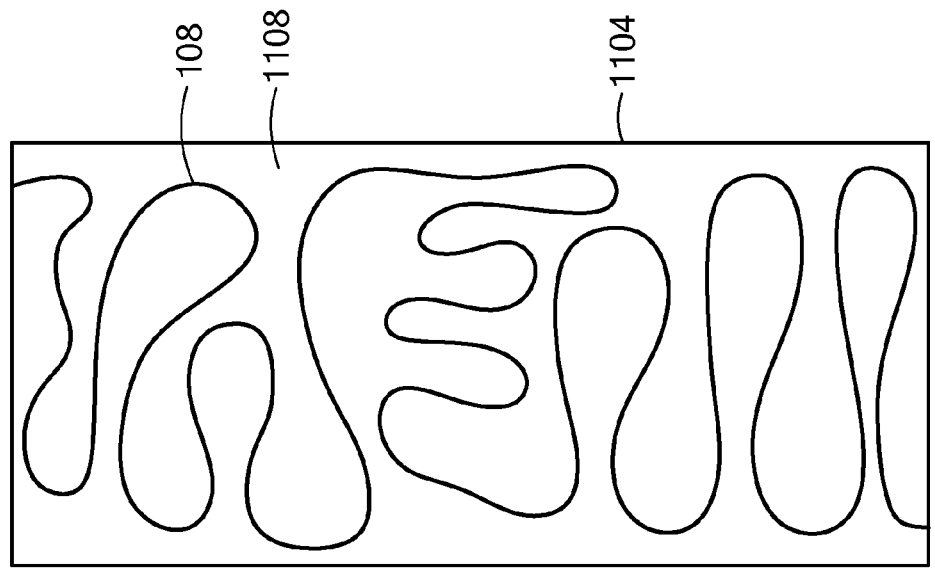
FIGS. 13 and 14 are alternate arrangements of a signal path in a sensor tape in accordance with embodiments of the present invention.

Still further, a meandering, i.e., randomly, or semi-randomly, arranged sole signal path may be provided as shown in FIG. 14. Such a meander may be chosen to provide a minimum necessary detection resolution.

Each embodiment of the present invention can be used to detect the presence or absence of an event such as, for example, a bullet hole in the pipeline 504 or thieves placing a "bleeder" tube into the pipeline 504 (intrusion events) or a corrosion induced leak or a corrosive hole forming in the pipeline 504 and leaking fluid (extrusion events). Similarly, an intrusion into a secured cargo container or an extrusion event, such as, radiation detection from within an enclosed space, may be detected.

In operation, the absence of an electrical or optical signal provides a self-monitoring feature that does not require initiating an active signal to interrogate a secured system in order to obtain a response. A fail-safe "always on" conducting signal that fails to be detected in a continuous manner indicates a "problem," be it the detection of an intrusion event or an extrusion event or failure of the system components such as its power supply. This detection information may be provided and monitored in real-time to enable either the determination of a location of an event at a specific pipe segment or the presence of a failed component in the sensor tape segment which, in effect, shuts the system down. Thus, a failed component is treated as an intrusion or extrusion event.

Figure 6:
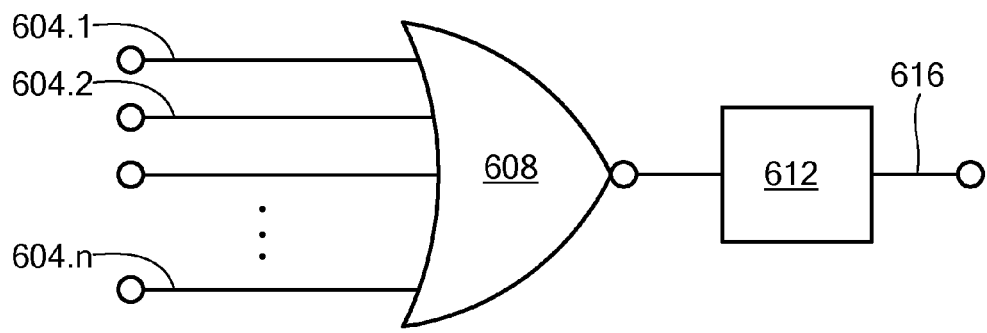
FIG. 6 is a block diagram of an intrusion/extrusion detection system in accordance with an embodiment of the present invention.

In one embodiment, an output 604.n of each respective tape segment or strip 100, 200 is fed to a NOR gate function 608 and then to a processor 612, such as shown in FIG. 6. In a normal non-alarm condition, a signal is received from each tape segment 100, 200 and is applied to the processor 612 to signify the normal state. If an incursion or excursion event occurs that causes a break in the signal path 108 of even a single wire of a tape segment 100, 200, the signal 604.n from that segment 100, 200 will cease, which will cause the NOR gate function 608 to present an alarm signal to the processor 612 which will produce an alarm output 616. One of ordinary skill in the art will understand that the NOR gate function 608 may be provided by discrete components or could be performed within the processor 612 if all output signals 604.n are provided to the processor 612.

Figure 7:
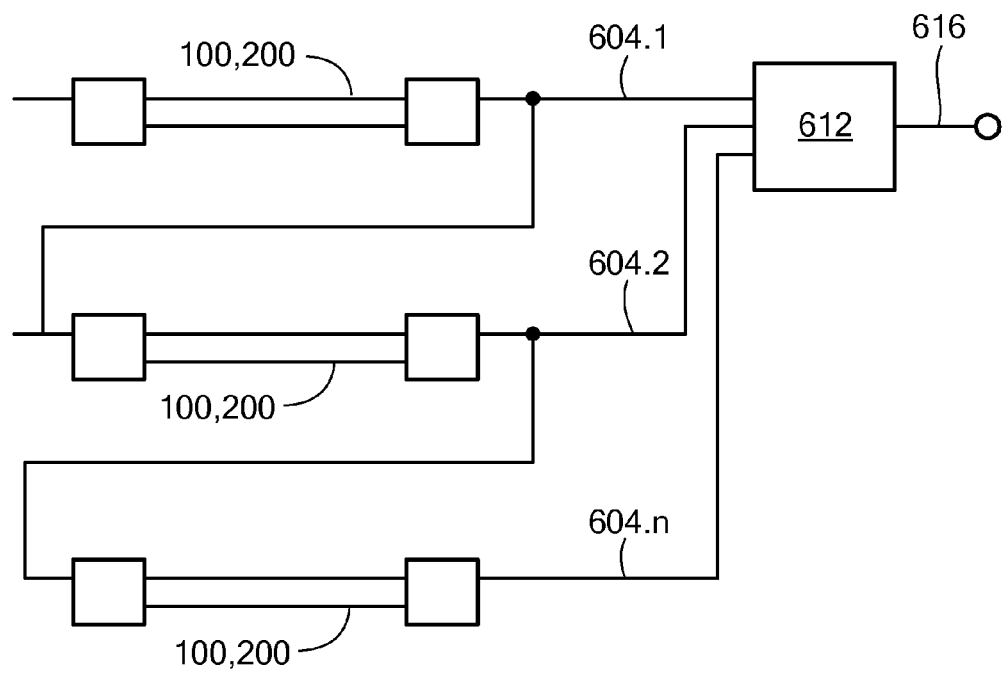
FIG. 7 is a block diagram of an intrusion/extrusion detection system in accordance with an embodiment of the present invention.

In another embodiment, the processor 612 can identify the tape segment where the alarm event has been detected and can provide other data as may be required or desirable. Referring now to FIG. 7, a number of sensor tapes 100, 200 are connected in series where the output signal 604.n of one is the input to the next. The output signal 604.n of each sensor tape is also submitted to the processor 612 to be processed as described above where the lack of an output signal indicates an event and the specific sensor tape 100, 200 that has detected the event can be determined.

Figure 8:
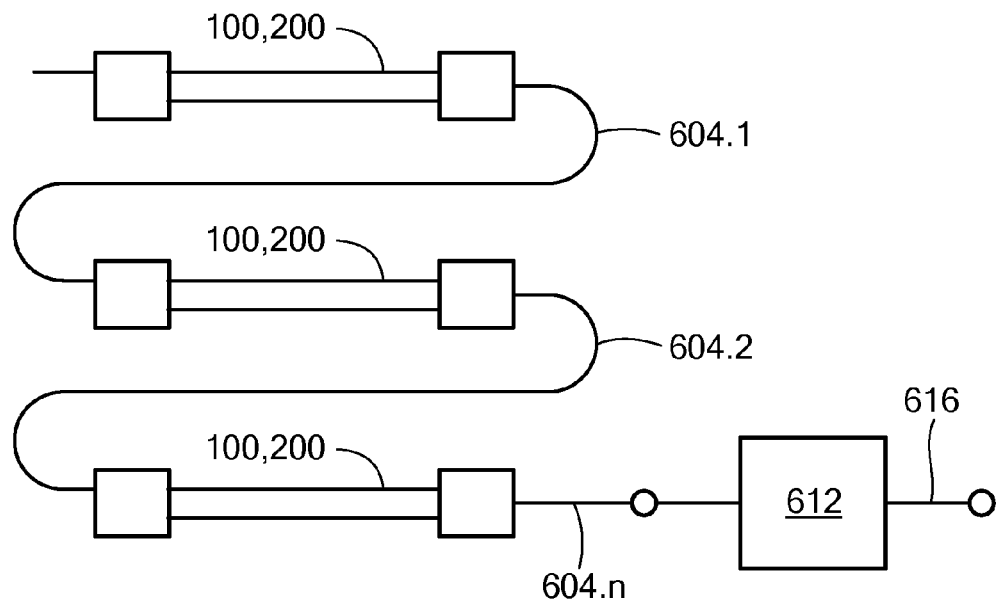
FIG. 8 is a block diagram of an intrusion/extrusion detection system in accordance with an embodiment of the present invention.

Alternately, where a number of sensor tapes 100, 200 are connected in series, as shown in FIG. 8, a single output 604.n may be provided to the processor 612. If the signal on the single output 604.n ceases, the processor 612 will raise the alarm output 616 as detecting an event although the location of the event, i.e., the specific sensor tape 100, 200 that detected the event, in this particular embodiment, cannot be determined.

Information regarding the alarm event can be transmitted to one or more local and/or remote receiving sites by any wired or wireless modality provided in conjunction with the processor 612.

Figure 10:
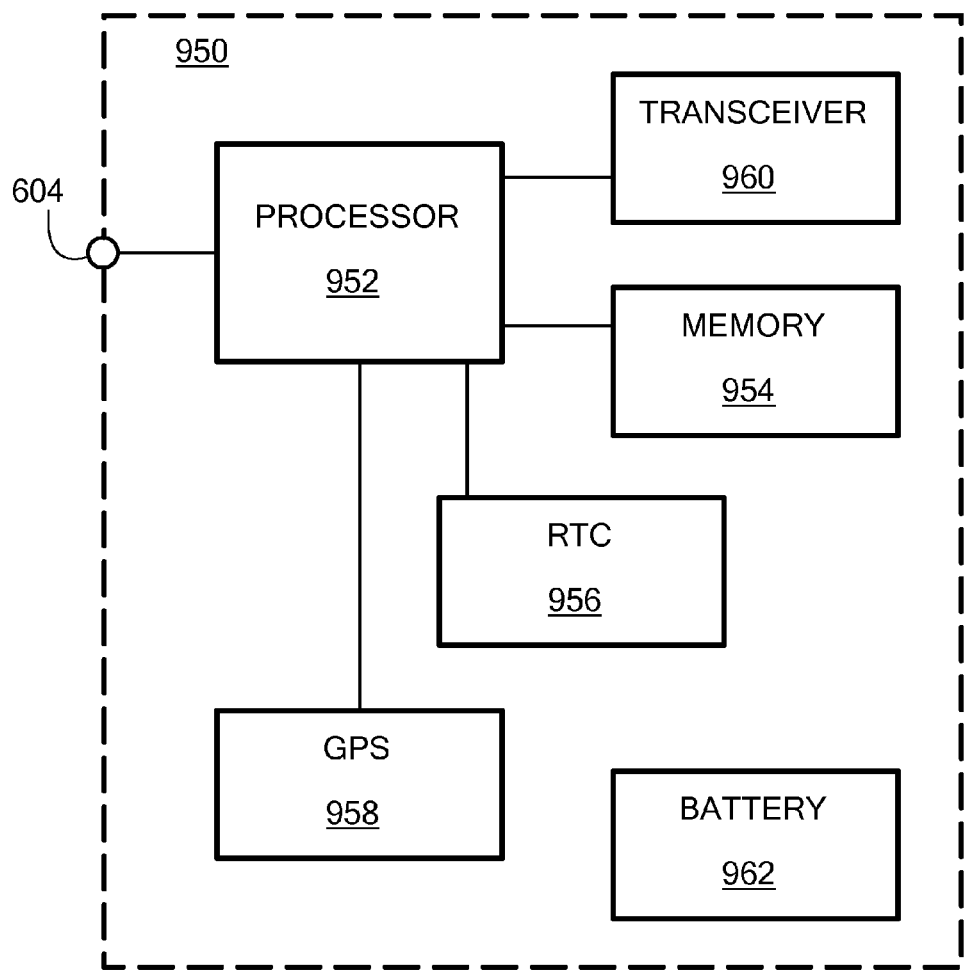
FIG. 10 is a block diagram of a system in accordance with an embodiment of the present invention.

As described above, each connector 112, 204 is provided to allow a signal to be passed along any length of pipeline desired by connecting the output electrical or optical signal from one end of a sensor tape 100, 200 corresponding to an individual pipe segment to the input connector of the next sensor tape 100, 200 corresponding to the next pipe segment. Alternately, each pipe segment comprising an individual unit within a pipeline system may have, in addition to connectors on both ends, a system 950, implemented as, for example, an integrated circuit device, which can have monitoring functions built into its microprocessor platform with associated software, as shown in FIG. 10. The system 950 may be integrated into a connector 112, 204.

The device 950 may include a processor 952 and a memory 954 that can hold data identifying a respective pipe segment in the pipeline system, such as a unique pipe segment address that allows for identification of the specific pipe segment where a detected problem has occurred. The device 950 can have a real-time clock 956 for time and date information that facilitates identification of the detected event. In addition, a GPS device 958 may be included to provide location information. Of course, if the location is static, i.e., not moving, then a GPS device may not be needed and the static location information can be stored in the memory 954. Alternatively, the device 950 can act as a node to transmit status data through any modality such as, for example, satellite, wire, wireless, and/or internet, for example, with an appropriately configured transceiver 960. The system may be powered by a battery 962 that can be charged by solar power, for example. A device such as the Snapdragon™ processor available from Qualcomm Incorporated may be used.

Further, in the application to a pipeline, as each pipe segment is installed in the pipeline, a real time test of conductivity of the sensor tape 100, 200 can be instituted for each electrical wire or optical fiber embedded in the tape strip as it is wrapped around the pipe segment. The test signal detected in this initial wrapping insures that any problems in connectivity are immediately detected in real-time to optimize cost and performance functions.

Still further, embodiments of the present invention allow for testing the integrity of an entire system and for detecting the falsification of the signal indicating that no incursion or excursion has been detected because of the fail-safe nature of the system and its binary output (signal/no-signal). If, for example, a third party were interfering with the output signal and had over-ridden it to always indicate a safe condition, the operator could test for this by turning off power to the sensors and determining whether or not the output of the system changes state. Of course, either the entire system could be turned off or only one or more of the sensor segments. If the output signal does not change in response to all, or part, of the system being shut down, then there may be some interference with the system in progress.

Embodiments of the present invention may also be made of materials and components that are meant to reduce the cost in order to make the tape sensor either disposable or for single-use. Thus, for example, the tape may be thinner, such as for packing applications, where removal of the tape when opening the package permanently renders the tape inoperative. In addition, the components within the connector may have less functionality, in order to reduce cost, and, therefore, lend themselves to disposable applications.

Known installations of detector sheets include a process of applying a resin and then having to wait for the resin to reach a point of tackiness for subsequent attachment of the sensor sheet. Advantageously, embodiments of the present invention simplify the fabrication and installation of a sensor system. As described above, the sensor tape 100, 200 has silicone rubber laminated or applied on both sides and forms a multi-layer tape. In one example, this might be provided as a roll of rubberized tape with the sensor sandwiched in the middle, for example, measuring 6 inches wide and 250 feet long to allow for use in a "spin wrap" process, well known to those in the pipeline insulation wrapping business, to rapidly encapsulate a pipe for a pipeline to be protected by the tamper proof tape to provide for detection of an intrusion/extrusion event.

Referring now to FIG. 15, a pipe 1504, which could be a gas well casing or similarly shaped object will have a plurality of circumferentially-placed (CP) sensor tapes 1508.1 . . . 1508.$n$ separately arranged around the circumference of the pipe 1504 and adjacent one another along the pipe 1504, i.e., longitudinally arranged and not helically positioned. The CP sensor tapes 1508.$n$ are arranged so as to effectively cover the entire outer surface area of the pipe 1504. The CP sensor tapes 1508.$n$ may be any one of the sensor tape types described above. A bus 1512 runs along the length of the pipe 1504 and each CP sensor tape 1508.$n$ is connected to the bus 1512.

In one embodiment, each CP sensor tape 1508.$n$ receives an input signal from, and provides an output signal to, the bus 1504. The bus 1504 may also provide power and any other necessary signals to each CP sensor tape 1508.$n$ as well as be in communication with, for example, a central monitoring station either by wired or wireless communications protocols. Alternately, each CP sensor tape 1508 may be self-contained and supplying only the output signal to the bus 1504.

Each CP sensor tape 1508.$n$ is uniquely identifiable, either by a unique address value programmed into the system 950 within a connector on the CP sensor tape 1508.$n$ or by its respective location along the bus 1512. Thus, the location of each CP sensor tape 1508.$n$ with respect to the length of the pipe 1504 is known.

In operation, when, for example, a rupture occurs in the wall of the pipe 1504 and gas is leaking out, the signal in a signal path of at least one of the CP sensor tapes 1508.$n$ will be disrupted. The loss of a signal will be detected by circuitry either on the communication bus 1512, and this condition will be conveyed to the central system, or the bus 1512 will only be a conduit for the output signal, or lack thereof, to reach the central system where the determination of a lost signal will be made. The circuitry on the bus 1512 will report the identifier of the failed sensor tape 1508.$n$ and the central system may determine where the breach is located. One of ordinary skill will understand that there are many different bus protocols that may be implemented for connection and communication among the bus 1512, the CP sensor tapes 1508.$n$ and the central system.

Once the reporting CP sensor tape 1508.$n$ is identified, and its location has been determined, repair operations can be started. One of ordinary skill in the art will understand that the embodiment shown in FIG. 15 will identify a circular "breach band" around the pipe and at a location along the length of the pipe 1504 within which the breach has occurred. This "breach band" will be as wide as the CP sensor tape 1508.$n$.

An embodiment that identifies the location around the circumference within the "breach band" will now be described with reference to FIG. 16. As shown, the plurality of CP sensor tapes 1508.$n$ are provided around the pipe 1504, similar to that shown in FIG. 15 and each is connected to the bus 1512 as already described.

Additionally, a plurality of longitudinally-positioned (LP) sensor tapes 1520.1 . . . 1520.$n$ are arranged around the circumference of the pipe 1504 over the CP sensor tapes 1508.$n$. The LP sensor tapes 1520.$n$ can be any one of the type of sensor tape described above. The LP sensor tapes 1520.$n$ are placed so as to cover the entire surface of the pipe 1504.

Alternatively, the LP sensor tapes 1520.$n$ may be placed first with the CP sensor tapes 1508.$n$ placed over the LP sensor tapes 1520.$n$.

Each LP sensor tape 1520.$n$ is connected to the bus 1512 and receives an input signal from, and provides an output signal to, the bus 1504. The bus 1504 may also provide power and any other necessary signals to each LP sensor tape 1520.$n$. Alternately, each LP sensor tape 1520 may be self-contained and supplying only the output signal to the bus 1504. Each LP sensor tape 1520.$n$ is uniquely identifiable, either by a unique address value programmed into the circuitry within a connector on the LP sensor tape 1520.$n$ or by its respective connection location to the bus 1512. Thus, the location of each LP sensor tape 1520.$n$ with respect to the circumference of the pipe 1504 is known.

In operation, when, for example, a rupture occurs in the wall of the pipe 1504 and gas is leaking out, the signal in a signal path in a CP sensor tape 1508.$n$ and an LP sensor tape 1520.$n$ will be disrupted. The loss of these two signals will be detected and the specific CP sensor tape 1508.$n$ and specific LP sensor tape 1520.$n$ will be identified. As a result, more precise coordinates of a breach, along the length and around the circumference, can be determined.

If, for example, each LP sensor tape is W inches wide, then an area of $W^2$ inches at a location along the length and around the circumference of the pipe 1504 has been identified as having a leak within it. This more specific locating function allows for repair operations being implemented more quickly and accurately.

Embodiments of the present invention produce a fail-safe, self-monitoring, reliable, durable and robust tape/fabric sensor system able to withstand the rigors of harsh environmental conditions such as experienced by a pipeline or cargo container. Embodiments of the present invention can be utilized in both aboveground and underground pipeline systems and can be applied as new construction in a factory or as a field installed retrofit.

Having thus described several features of at least one embodiment of the present invention, it is to be appreciated that various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A sensor security detector tape for wrapping around an object to be protected, comprising:
- a material strip having a predetermined width and a predetermined length and first and second ends;
- a plurality of separate and parallel electrical signal paths arranged along the predetermined length of the material strip, each signal path having a first end at one end of the predetermined length of the material strip and a second end at the other end of the predetermined length of the material strip and operative in a non-alarm condition to carry a signal;
- a first connector coupled to each first end of the plurality of signal paths and connecting adjacent pairs of the first ends of the plurality of signal paths to one another;
- a second connector coupled to each second end of the plurality of signal paths and connecting adjacent pairs of the second ends of the plurality of signal paths to one another;
- wherein the connected pairs of first ends and second ends by the first and second connectors, respectively, establish a single continuous electrical signal path;
- the first connector operative to couple an electrical signal from a signal source for transmission over the single continuous signal path;
- the second connector operative to couple the electrical signal transmitted over the single continuous signal path to a signal detector; and
- wherein a break in any of the signal paths causes a loss of the electrical signal transmitted over the single continuous signal path and indicative of an alarm condition.

2. The sensor security detector tape of claim 1, further comprising:
- means for inputting a signal into the single continuous signal path via the first connector; and
- means for detecting the signal from the single continuous signal path coupled from, the second connector.

3. The sensor security detector tape of claim, 1 wherein each of the signal paths is an electrical wire and the first and second connectors couple the first and second ends of the signal paths to carry an electrical signal.

4. The sensor security detector tape of claim 1, wherein the material strip is a fabric and each of the signal paths is woven into the fabric.

5. The sensor security detector tape of claim 1, further comprising:
- a layer of adhesive material disposed on a first surface of the material strip,
- wherein each of the signal paths is disposed in the adhesive material layer.

6. The sensor security detector tape of claim 5, further comprising:
- a releasable material layer disposed over the adhesive material layer.

7. The sensor security detector tape of claim 1, wherein:
the predetermined width is in a range of 5-7 inches; and
the predetermined length is in a range of 250-300 feet.

8. The sensor security detector tape of claim, 1 further comprising:
- a first flexible protection layer disposed on a first side of the material strip; and
- a second flexible protection layer disposed on the second side of the material strip.

* * * * *